United States Patent
Nakamura (10) Patent No.: US 12,094,584 B2
(45) Date of Patent: Sep. 17, 2024

(54) DOCUMENT CREATION SUPPORT APPARATUS, DOCUMENT CREATION SUPPORT METHOD, AND PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/879,784

(22) Filed: Aug. 3, 2022

(65) Prior Publication Data

US 2022/0375562 A1 Nov. 24, 2022

Related U.S. Application Data

(63) Continuation of application No. PCT/JP2021/004835, filed on Feb. 9, 2021.

(30) Foreign Application Priority Data

Feb. 10, 2020 (JP) ................. 2020-020866

(51) Int. Cl.
*G16H 15/00* (2018.01)
*G06F 3/0482* (2013.01)
(Continued)

(52) U.S. Cl.
CPC ........... *G16H 15/00* (2018.01); *G06F 3/0482* (2013.01); *G06F 40/166* (2020.01);
(Continued)

(58) Field of Classification Search
CPC .................................................. G06F 40/166
See application file for complete search history.

(56) References Cited

U.S. PATENT DOCUMENTS 7,894,676 B2   2/2011  Iizuka et al.
10,909,681 B2 * 2/2021  Hsiao et al. .......... G06T 7/0016
(Continued)

FOREIGN PATENT DOCUMENTS

JP   2009082443    4/2009
JP   2009259000   11/2009
(Continued)

OTHER PUBLICATIONS

"International Search Report (Form PCT/ISA/210) of PCT/JP2021/004835," mailed on May 11, 2021, with English translation thereof, pp. 1-5.
(Continued)

*Primary Examiner* — James J Debrow
(74) *Attorney, Agent, or Firm* — JCIPRNET (57) ABSTRACT

An analysis unit (13) specifies properties of a feature portion included in an image for each of a plurality of predetermined property items. A text generation unit (14) generates a plurality of texts such that a combination of the property items is different between the plurality of texts. In a case where any one of the plurality of texts is selected, an association data generation unit (16) generates association data in which a selection item, which is a property item corresponding to the property described in the selected text, and a property specifying result are associated with each other. In a case where the specified property and the property specifying result included in the association data match, the text generation unit (14) generates a priority text describing the property specified for the same property item as the selection item associated with the property specifying result as one of the plurality of texts.

7 Claims, 10 Drawing Sheets

(51) Int. Cl.
*G06F 40/166* (2020.01)
*G06T 7/00* (2017.01)
*G06V 20/70* (2022.01)

(52) U.S. Cl.
CPC ............ *G06T 7/0012* (2013.01); *G06V 20/70* (2022.01); *G06T 2207/10081* (2013.01); *G06T 2207/20081* (2013.01); *G06T 2207/30096* (2013.01); *G06V 2201/03* (2022.01)

(56) References Cited

U.S. PATENT DOCUMENTS

| | | | |
|---|---|---|---|
| 2009/0274384 A1* | 11/2009 | Jakobovits | ............... G06K 9/40 |
| 2010/0189366 A1 | 7/2010 | Iizuka et al. | |
| 2011/0164064 A1* | 7/2011 | Tanaka et al. | ............ G06T 7/00 |
| 2019/0139218 A1* | 5/2019 | Song et al. | ........... G06T 7/0012 |
| 2019/0279751 A1 | 9/2019 | Nakamura et al. | |
| 2020/0160982 A1* | 5/2020 | Gurson et al. | ......... G16H 30/40 |

FOREIGN PATENT DOCUMENTS

| | | |
|---|---|---|
| JP | 2011100254 | 5/2011 |
| JP | 2017029411 | 2/2017 |
| JP | 2017191520 | 10/2017 |
| JP | 2019153250 | 9/2019 |
| WO | 2009041586 | 4/2009 |

OTHER PUBLICATIONS

"Written Opinion of the International Searching Authority (Form PCT/ISA/237)" of PCT/JP2021/004835, mailed on May 11, 2021, with English translation thereof, pp. 1-6.

"Office Action of Japan Counterpart Application", issued on Sep. 12, 2023, with English translation thereof, p. 1-p. 3.

* cited by examiner

| PROPERTY ITEM | PROPERTY SPECIFYING RESULT |
|---|---|
| POSITION | LEFT UPPER LOBE |
| PRESENCE OR ABSENCE OF PLEURAL INVAGINATION | PLEURAL INVAGINATION + |
| PRESENCE OR ABSENCE OF IRREGULAR MARGIN | IRREGULAR MARGIN + |
| PRESENCE OR ABSENCE OF SPICULA | SPICULA + |
| TYPE OF DISEASE | TUMOR |

T2: TUMOR WITH PLEURAL INVAGINATION IS FOUND IN LEFT UPPER LOBE.

109

| PROPERTY SPECIFYING RESULT | SELECTION ITEM |
|---|---|
| LEFT UPPER LOBE PLEURAL INVAGINATION + IRREGULAR MARGIN + SPICULA + TUMOR | POSITION PRESENCE OR ABSENCE OF PLEURAL INVAGINATION TYPE OF DISEASE |

DOCUMENT CREATION SUPPORT APPARATUS, DOCUMENT CREATION SUPPORT METHOD, AND PROGRAM

CROSS-REFERENCE TO RELATED APPLICATION

This application is a continuation application of International Application No. PCT/JP2021/004835, filed Feb. 9, 2021, the disclosure of which is incorporated herein by reference in its entirety. Further, this application claims priority from Japanese Patent Application No. 2020-020866 filed on Feb. 10, 2020, the disclosures of which is incorporated herein by reference in its entirety.

BACKGROUND

1. Technical Field

Disclosed technologies relate to a document creation support apparatus, a document creation support method, and a program.

2. Description of the Related Art

The following technologies are known as technologies related to a document creation support apparatus that generates texts that can be applied to documents such as interpretation reports based on medical images. For example, JP2009-82443A describes a diagnostic support apparatus comprising a storage unit, an acquisition unit, a search unit, and a generation unit, the storage unit being configured to store image feature information and comments on findings of an interpretation result in association with each other, the acquisition unit being configured to acquire image feature information of a region of interest designated in an image to be interpreted, the search unit being configured to search for image feature information similar to the image feature information acquired by the acquisition unit from the storage unit and acquire comments on findings that are stored in association with the searched image feature information from the storage unit, and the generation unit being configured to generate comments on findings of an interpretation of the designated region of interest by changing the description of the comments on findings acquired by the search unit based on the image feature information of the region of interest acquired by the acquisition unit.

Further, JP2009-259000A describes a document creation support apparatus comprising an operation input control unit, a registration unit, a search unit, and a display control unit, the operation input control unit being configured to select a desired term from a plurality of terms prepared in advance, select terms to be used as a sentence from a fixed phrase generated according to a combination of selected terms or input candidates, receive corrections to the selected sentence, and use the corrected sentence as a correction sentence, the registration unit being configured to associate a combination of terms selected by the operation input control unit with the correction sentence and registering it in a dictionary, the search unit being configured to search the dictionary for a correction sentence in which the combination of terms selected by the operation input control unit and a combination of terms associated with the registration unit match, and the display control unit being configured to display the correction sentence found by the search unit as input candidates for the sentence selected by the operation input control unit.

SUMMARY

A text that is automatically generated based on the medical image may be missing important information or may contain non-important information, and thus a text that matches the user's request may not always be generated. In order to deal with this, it is conceivable to present a plurality of candidate texts having different descriptions and to allow the user to select a text that matches the user's request from among the plurality of candidate texts. In this case, it is preferable that the plurality of candidate texts have a variety of description contents. As a result, there is a high likelihood that texts that match the user's request are included in the plurality of candidate texts. Further, by reflecting the tendency of the description content of the text selected by the user in the subsequent text generation, there is a higher likelihood that texts that match the user's request are included in the plurality of candidate texts.

The disclosed technology has been made in view of the above points, and an object thereof is to increase a likelihood that a text that matches a user's request is generated in a case of automatically generating texts based on images.

A document creation support apparatus according to the disclosed technology is a document creation support apparatus comprising at least one processor. The processor is configured to specify properties of a feature portion included in an image for each of a plurality of predetermined property items, in a case where a plurality of different texts describing at least one of the specified properties are generated, generate the plurality of texts such that a combination of property items corresponding to the properties described in each of the plurality of texts is different between the plurality of texts, in a case where any one of the plurality of texts is selected, generate association data in which a selection item, which is a property item corresponding to a property described in the selected text, and a property specifying result, which is a result of specifying the property for each of the plurality of property items in a case of generating a plurality of texts including the selected text, are associated with each other, and in a case where the property specified for each of the plurality of property items and the property specifying result included in the association data match, generate a priority text describing the property specified for the same property item as the selection item associated with the property specifying result as one of the plurality of texts.

The processor may be configured to, in a case where each of the plurality of texts is displayed on a display screen, perform control such that the priority text is displayed in an identifiable manner from other texts. The processor may be configured to perform control such that the plurality of texts are displayed in a line in a vertical direction of the display screen to locate the priority text at the top of the display screen. Further, the processor may be configured to perform control such that the priority text is highlighted. In addition, the processor may be configured to generate the association data each time any one of the plurality of texts is selected, and store the generated association data in a storage unit.

A document creation support method according to the disclosed technology comprises: specifying properties of a feature portion included in an image for each of a plurality of predetermined property items; in a case where a plurality of different texts describing at least one of the specified properties are generated, generating the plurality of texts such that a combination of property items corresponding to the properties described in each of the plurality of texts is different between the plurality of texts; in a case where any one of the plurality of texts is selected, generating association data in which a selection item, which is a property item corresponding to a property described in the selected text, and a property specifying result, which is a result of specifying the property for each of the plurality of property items in a case of generating a plurality of texts including the selected text, are associated with each other; and in a case where the property specified for each of the plurality of property items and the property specifying result included in the association data match, generating a priority text describing the property specified for the same property item as the selection item associated with the property specifying result as one of the plurality of texts.

A program according to the disclosed technology is a program for causing a computer to execute a process comprising: specifying properties of a feature portion included in an image for each of a plurality of predetermined property items; in a case where a plurality of different texts describing at least one of the specified properties are generated, generating the plurality of texts such that a combination of property items corresponding to the properties described in each of the plurality of texts is different between the plurality of texts; in a case where any one of the plurality of texts is selected, generating association data in which a selection item, which is a property item corresponding to a property described in the selected text, and a property specifying result, which is a result of specifying the property for each of the plurality of property items in a case of generating a plurality of texts including the selected text, are associated with each other; and in a case where the property specified for each of the plurality of property items and the property specifying result included in the association data match, generating a priority text describing the property specified for the same property item as the selection item associated with the property specifying result as one of the plurality of texts.

According to the disclosed technology, it is possible to increase a likelihood that a text that matches a user's request is generated in a case of automatically generating texts based on images.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the disclosed technology will be described with reference to the drawings. In each drawing, substantially the same or equivalent components or portions are designated by the same reference numerals.

FIRST EMBODIMENT

Figure 1:
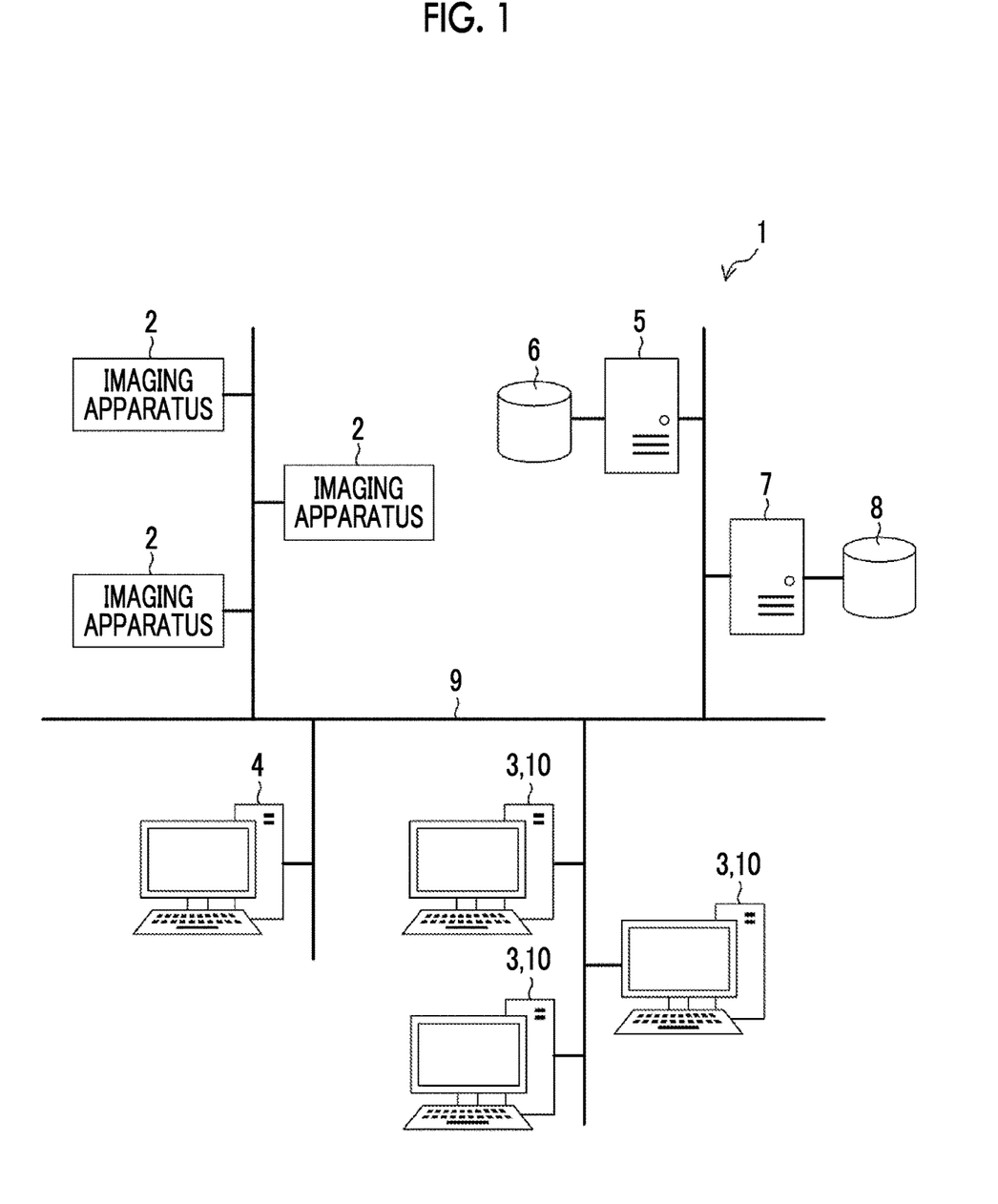
FIG. 1 is a diagram showing a schematic configuration of a medical information system according to an embodiment of the disclosed technology.

FIG. 1 is a diagram showing a schematic configuration of a medical information system 1 to which a document creation support apparatus according to an embodiment of the disclosed technology is applied. The medical information system 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

In the medical information system 1, a plurality of imaging apparatuses 2, a plurality of interpretation workstations (WS) 3 that are interpretation terminals, a medical department workstation (WS) 4, an image server 5, an image database 6, an interpretation report server 7, and an interpretation report database 8 are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 9 or in a network storage in a state in which it can be accessed from the outside, and is downloaded to and installed on the computer in response to a request.

The imaging apparatus 2 is an apparatus that generates a medical image showing a diagnosis target part of the subject by imaging the diagnosis target part. The imaging apparatus 2 may be, for example, a simple X-ray imaging apparatus, a CT apparatus, an MRI apparatus, a positron emission tomography (PET) apparatus, and the like. A medical image generated by the imaging apparatus 2 is transmitted to the image server 5 and is saved therein.

The medical department WS 4 is a computer used by a doctor in a medical department to observe a medical image in detail, view an interpretation report, create an electronic medical record, and the like, and includes a processing apparatus, a display apparatus such as a display, and an input apparatus such as a keyboard and a mouse. In the medical department WS 4, each process such as creating a medical record (electronic medical record) of a patient, requesting to view an image from the image server 5, displaying a medical image received from the image server 5, automatically detecting or highlighting suspected disease regions in the medical image, requesting to view an interpretation report from the interpretation report server 7, and displaying the interpretation report received from the interpretation report server 7 is performed by executing a software program for each process.

The image server 5 is a general-purpose computer on which a software program that provides a function of a database management system (DBMS) is installed. The image server 5 comprises the image database 6 including a storage. The image database 6 may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the imaging apparatus 2, the image server 5 prepares the medical image in a format for a database and registers the medical image in the image database 6.

Image data of the medical image acquired by the imaging apparatus 2 and accessory information attached to the image data are registered in the image database 6. The accessory information includes, for example, an image identification (ID) for identifying each medical image, a patient ID for identifying a patient who is a subject, an examination ID for identifying an examination content, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (imaging part), imaging information (an imaging protocol, an imaging sequence, an imaging method, imaging conditions, the presence or absence of the use of a contrast medium, and the like), and information such as a series number or a collection number when a plurality of medical images are acquired in one examination. In addition, in a case where a viewing request from the interpretation WS 3 is received through the network 9, the image server 5 searches for a medical image registered in the image database 6 and transmits the searched for medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

In the interpretation WS 3, each process such as requesting to view a medical image from the image server 5, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting to register and view the interpretation report from the interpretation report server 7, and displaying the interpretation report received from the interpretation report server 7 is performed by executing a software program for each process. The interpretation WS 3 encompasses the document creation support apparatus 10 to be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
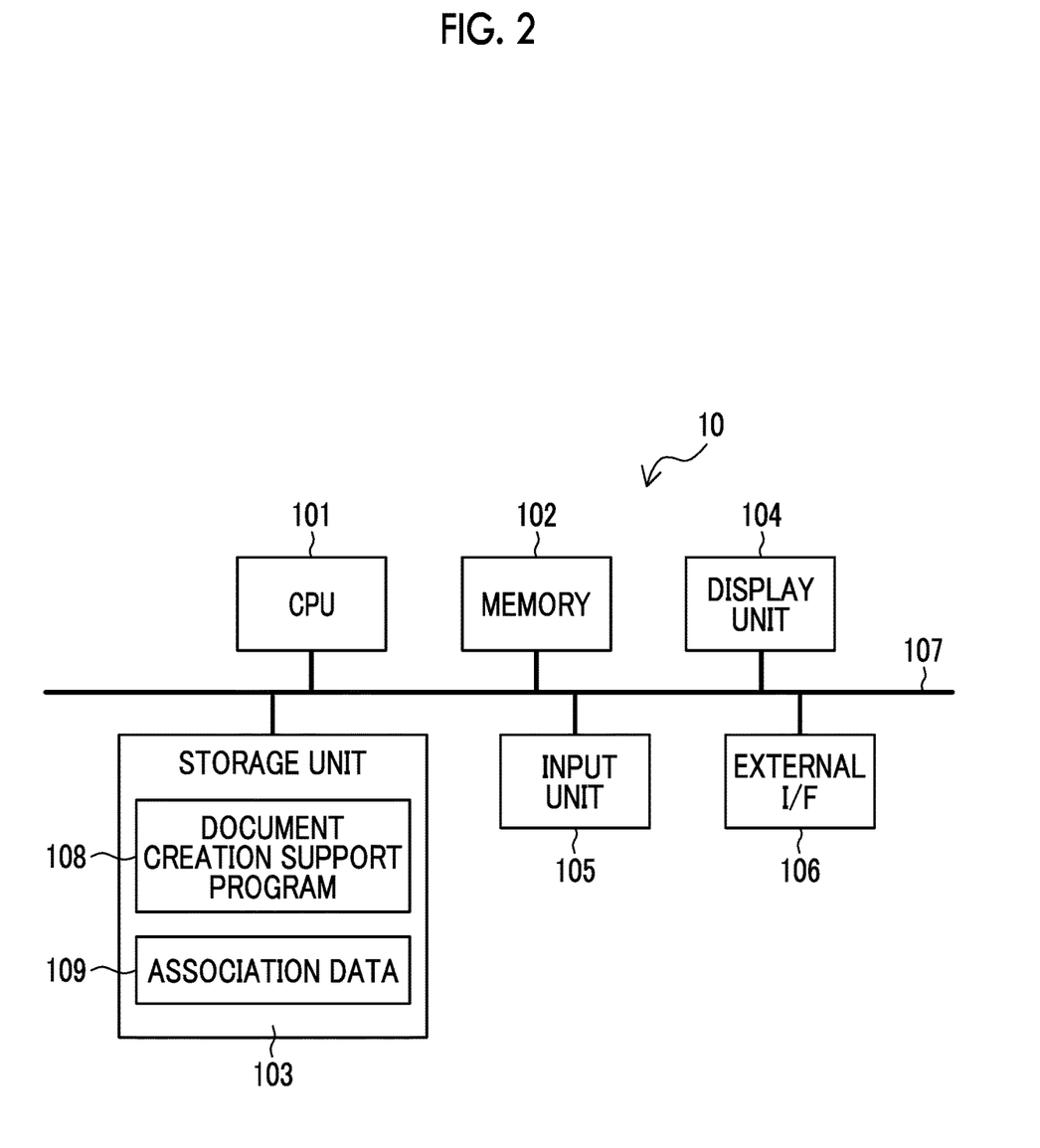
FIG. 2 is a diagram showing an example of a hardware configuration of a document creation support apparatus according to an embodiment of the disclosed technology.

FIG. 2 is a diagram showing an example of the hardware configuration of the document creation support apparatus 10. The document creation support apparatus 10 includes a central processing unit (CPU) 101, a memory 102, a storage unit 103, a display unit 104 such as a liquid crystal display, an input unit 105 such as a keyboard and a mouse, and an external interface (I/F) 106. The input unit 105 may be provided with a microphone that receives voice input. The CPU 101, the memory 102, the storage unit 103, the display unit 104, the input unit 105, and the external I/F 106 are connected to a bus 107. The document creation support apparatus 10 is connected to the network 9 of the medical information system 1 via the external I/F 106. The CPU 101 is an example of a processor in the disclosed technology.

The storage unit 103 is realized by a hard disk drive (HDD), a solid state drive (SSD), a flash memory, or the like. A document creation support program 108 is stored in the storage unit 103. The document creation support program 108 is recorded on a recording medium such as a DVD or a CD-ROM, and distributed, and is installed on the document creation support apparatus 10 from the recording medium. Alternatively, the document creation support program 108 is stored in a storage apparatus of a server computer connected to the network or in a network storage in a state in which it can be accessed from the outside, and is downloaded to and installed on the document creation support apparatus 10 in response to a request. The CPU 101 reads out the document creation support program 108 from the storage unit 103, loads the read document creation support program 108 into the memory 102, and executes the loaded document creation support program 108. Further, association data 109 is stored in the storage unit 103. The details of the association data 109 will be described later.

Figure 3:
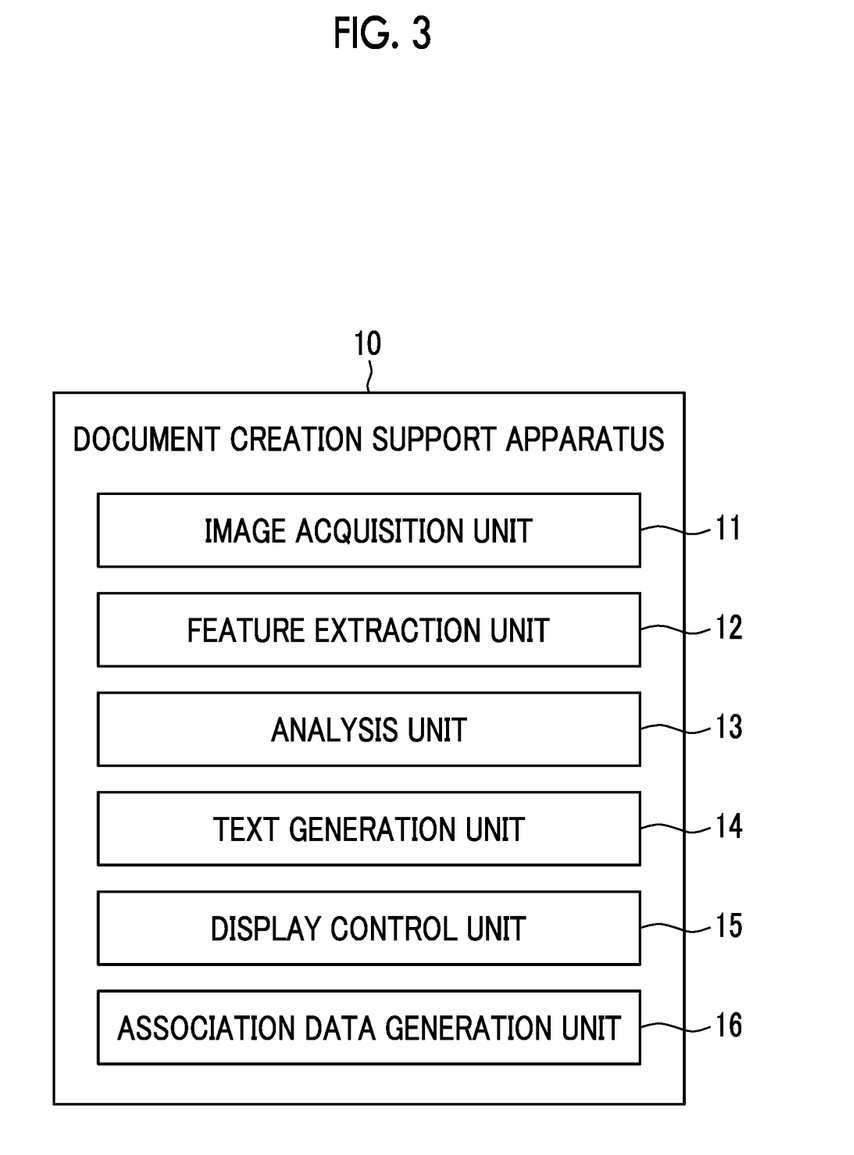
FIG. 3 is a functional block diagram showing an example of a functional configuration of the document creation support apparatus according to an embodiment of the disclosed technology.

FIG. 3 is a functional block diagram showing an example of the functional configuration of the document creation support apparatus 10. The document creation support apparatus 10 includes an image acquisition unit 11, a feature extraction unit 12, an analysis unit 13, a text generation unit 14, a display control unit 15, and an association data generation unit 16. The CPU 101 executes the document creation support program 108, so that the document creation support apparatus 10 functions as the image acquisition unit 11, the feature extraction unit 12, the analysis unit 13, the text generation unit 14, the display control unit 15, and the association data generation unit 16.

The image acquisition unit 11 acquires a medical image to be diagnosed (hereinafter referred to as a diagnosis target image). The diagnosis target image is saved in the image database 6, is transmitted from the image database 6 to the document creation support apparatus 10 in response to a request from the document creation support apparatus 10 (interpretation workstation 3), and is saved in the storage unit 103. The image acquisition unit 11 acquires the diagnosis target image saved in the storage unit 103. The image acquisition unit 11 may directly acquire the diagnosis target image saved in the image database 6 from the image database 6. In the following, a case where the diagnosis target image is a chest CT image will be described as an example.

Figure 4:
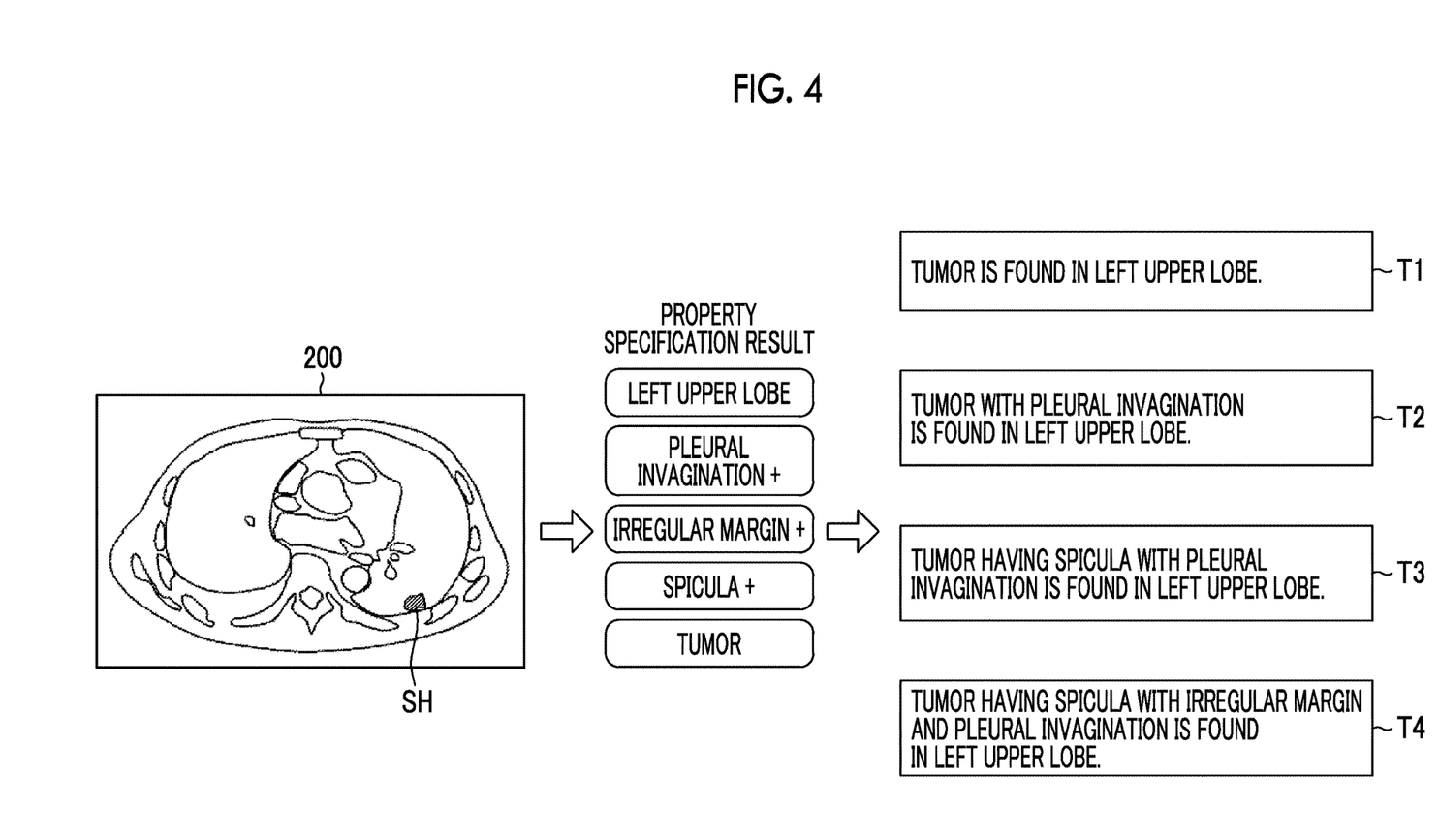
FIG. 4 is a diagram for describing a function of the document creation support apparatus according to an embodiment of the disclosed technology.

The feature extraction unit 12 extracts a shadow where a disease such as a nodule or tumor is suspected (hereinafter referred to as an abnormal shadow) as a feature portion from the diagnosis target image acquired by the image acquisition unit 11. The feature extraction unit 12 may extract an abnormal shadow using, for example, a trained model trained by machine learning such as deep learning. The above-mentioned trained model is trained by machine learning using, for example, a plurality of combinations of a medical image including an abnormal shadow and information specifying a region in the image in which the abnormal shadow is present as training data. The above-mentioned trained model uses a medical image as an input and outputs a result of specifying an abnormal shadow region in the medical image. FIG. 4 shows an example in which an abnormal shadow SH is extracted from a diagnosis target image 200.

The analysis unit 13 analyzes the abnormal shadow extracted by the feature extraction unit 12 to specify the properties of the abnormal shadow for each of a plurality of predetermined property items. Examples of the property items specified for the abnormal shadow include the position, the presence or absence of spicula, the presence or absence of an irregular margin, the presence or absence of pleural invagination, and the type of disease in the corresponding abnormal shadow.

The analysis unit 13 may specify the property of an abnormal shadow using, for example, a trained model trained by machine learning such as deep learning. The above-mentioned trained model is trained by machine learning using, for example, a plurality of combinations of a medical image including an abnormal shadow and a property label representing the property of the abnormal shadow as training data. The above-mentioned trained model uses a medical image as an input, and outputs a property score derived for each property item in the abnormal shadow included in the medical image. The property score is a score indicating the prominence of the property for the property item. The property score takes a value of 0 or more and 1 or less, for example, and the larger the value of the property score, the more remarkable the property.

For example, in a case where the property score for "the presence or absence of spicula", which is one of property items of an abnormal shadow, is, for example, 0.5 or more, the analysis unit 13 specifies that the property for "the presence or absence of spicula" of the corresponding abnormal shadow is "with spicula (positive)", and in a case where the property score for "the presence or absence of spicula" is less than, for example, 0.5, the analysis unit 13 specifies that the property for the "presence or absence of spicula" of the corresponding abnormal shadow is "no spicula (negative)". The threshold value 0.5 used for property determination is merely an example, and is set to an appropriate value for each property item.

FIG. 4 shows an example in which "left upper lobe", "pleural invagination+", "irregular margin+", "spicula+", and "tumor" are specified as the properties of each property item of the abnormal shadow SH extracted from a diagnosis target image 200. The "+" notation in the specified property indicates that the property is positive.

The text generation unit 14 generates, as candidate texts, a plurality of different texts describing the properties of the abnormal shadow for the abnormal shadows extracted by the feature extraction unit 12. The text generation unit 14 generates a plurality of texts such that at least one of the properties for each of a plurality of property items specified by the analysis unit 13 is described in each text. The text generation unit 14 generates the plurality of texts such that a combination of property items corresponding to the properties described in each of the plurality of texts is different between the plurality of texts.

FIG. 4 shows an example in which the text generation unit 14 generates four different texts describing the properties of the abnormal shadow SH. The text generation unit 14 generates a first text T1 including a description "A tumor is found in the left upper lobe" based on, for example, "left upper lobe" and "tumor" among the properties specified for each of the plurality of property items. Further, the text generation unit 14 generates a second text T2 including a description "A tumor with pleural invagination is found in the left upper lobe" based on, for example, "left upper lobe", "pleural invagination+", and "tumor" among the properties specified for each of the plurality of property items. Further, the text generation unit 14 generates a third text T3 including a description "A tumor having spicula with pleural invagination is found in the left upper lobe" based on, for example, "left upper lobe", "pleural invagination+", "spicula+", and "tumor" among the properties specified for each of the plurality of property items. Further, the text generation unit 14 generates a fourth text T4 including a description "A tumor having spicula with an irregular margin and pleural invagination is found in the left upper lobe" based on, for example, "left upper lobe", "pleural invagination+", "irregular margin+", "spicula+", and "tumor" among the properties specified for each of the plurality of property items.

In this way, the text generation unit 14 generates the plurality of texts such that at least one of the properties specified for each of a plurality of predetermined property items is described in each of the plurality of texts and a combination of property items corresponding to the properties described in each of the plurality of texts is different between the plurality of texts. The number of texts generated by the text generation unit 14 may be 3 or less, or 5 or more.

Further, in a case where a property specified for each of the plurality of property items and a property specifying result included in the association data 109 stored in the storage unit 103 match, the text generation unit 14 generates a priority text to be described later as one of a plurality of texts.

Figure 5:
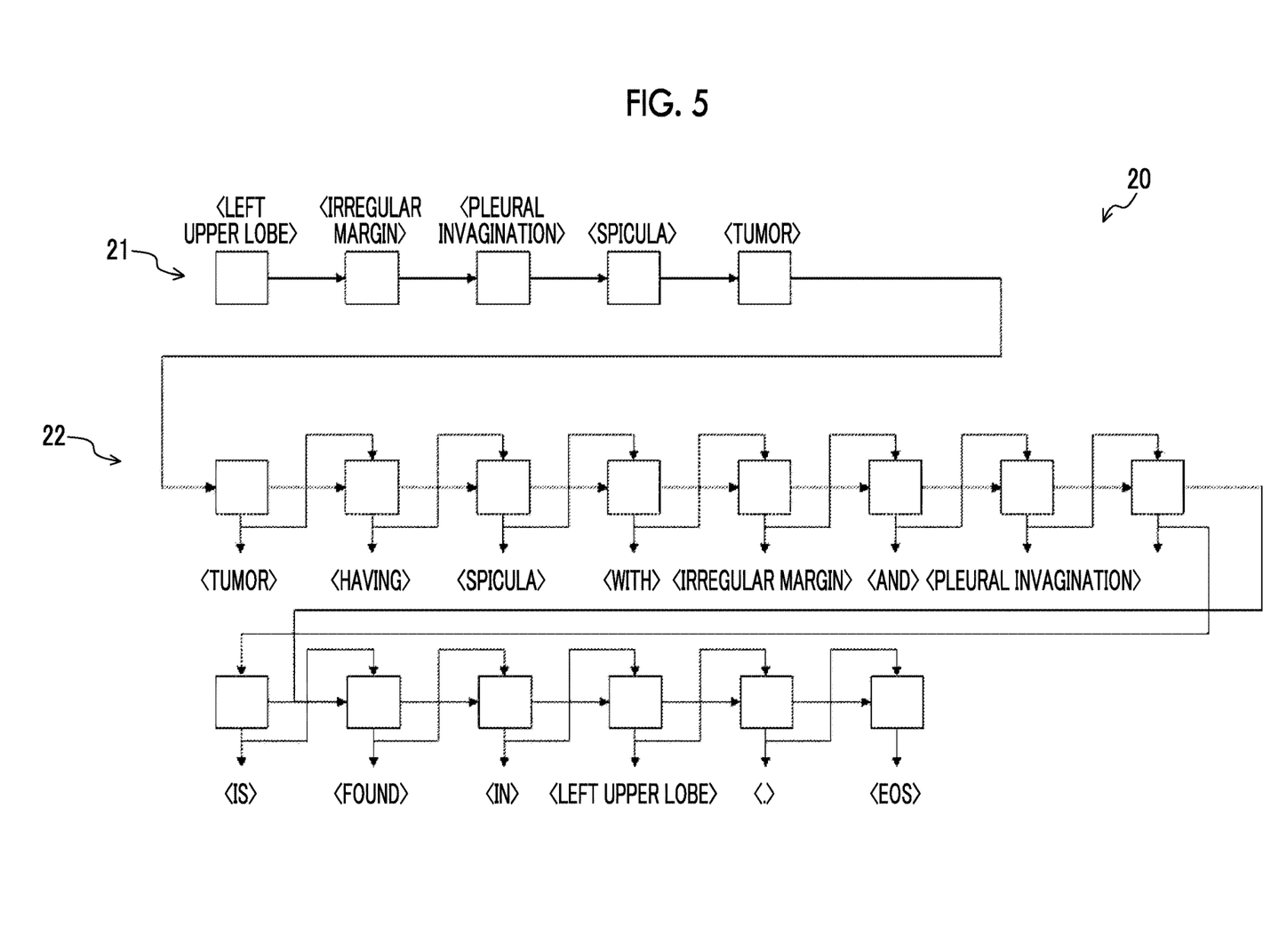
FIG. 5 is a diagram schematically showing an example of a configuration of a recurrent neural network constituting a text generation unit according to an embodiment of the disclosed technology.

The text generation unit 14 includes a recurrent neural network trained to create a text from the input words. FIG. 5 is a diagram schematically showing a configuration of a recurrent neural network. As shown in FIG. 5, the recurrent neural network 20 includes an encoder 21 and a decoder 22. Characters corresponding to the property specified by the analysis unit 13 are input to the encoder 21. For example, in a case where the text generation unit 14 generates the fourth text T4 illustrated in FIG. 4, "left upper lobe", "irregular margin", "pleural invagination", "spicula", and "tumor", which are characters of the properties specified by the analysis unit 13, are input to the encoder 21. The decoder 22 has been trained to document the words input to the encoder 21, and from the above input words, the fourth text T4 "A tumor having spicula with an irregular margin and pleural invagination is found in the left upper lobe" is generated. In FIG. 5, "EOS" indicates the end of the sentence (End Of Sentence).

Figure 6:
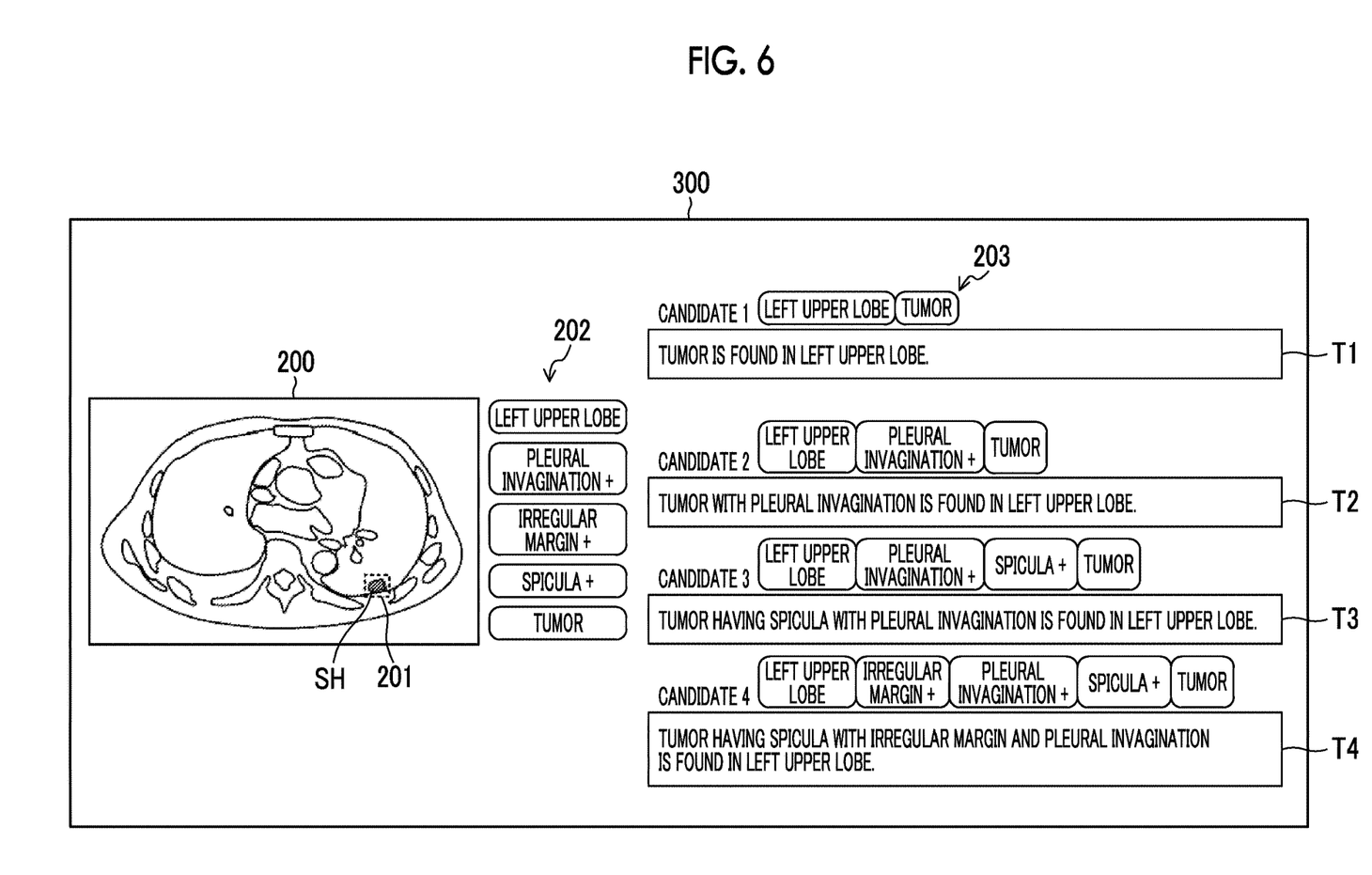
FIG. 6 is a diagram showing an example of a display mode of information displayed on a display screen according to an embodiment of the disclosed technology.

The display control unit 15 performs control such that the plurality of texts generated by the text generation unit 14 are displayed on the display unit 104. FIG. 6 is a diagram showing an example of a display mode of information displayed on a display screen 300 of the display unit 104 under the control of the display control unit 15. As shown in FIG. 6, the first to fourth texts T1 to T4 generated by the text generation unit 14 are displayed on the display screen 300. In addition, the diagnosis target image 200 including the abnormal shadow SH corresponding to the first to fourth texts T1 to T4 is displayed on the display screen 300. The diagnosis target image 200 may be provided with a mark 201 indicating the position of the abnormal shadow SH. In addition, on the display screen 300, a property label 202 indicating the properties of each property item specified for the abnormal shadow SH is displayed. Further, in the vicinity of each of the first to fourth texts T1 to T4, a property label 203 indicating the property described in the text is displayed. The user can select any one of the plurality of texts displayed on the display screen 300 and use the selected text as a part or all of the document (interpretation report) created by the user. The text can be selected, for example, by clicking the display region of the text to be selected with a pointer.

Further, in a case where the priority text is included in the plurality of texts generated by the text generation unit 14, the display control unit 15 displays the priority text in an identifiable manner from other texts. The display mode of the priority text will be described later.

The association data generation unit 16 generates the association data 109 in a case where any one of the plurality of texts generated by the text generation unit 14 is selected. The association data 109 is data in which a selection item, which is a property item corresponding to a property described in the text selected by the user, and a property specifying result, which is a result of specifying the property for each of the plurality of property items in a case of generating a plurality of texts including the text selected by the user, are associated with each other. The association data generation unit 16 stores the generated association data 109 in the storage unit 103.

As described above, for the abnormal shadow included in the diagnosis target image, the property is specified for each of the plurality of predetermined property items by the analysis of the analysis unit 13. On the other hand, a document (interpretation report) created by a user often describes only the properties for some property items that the user deems necessary. In this case, it is considered that there is a correlation between the property specifying result, which is the result of the property specified for each of the plurality of property items, and the property item that the user wants to include in the document (interpretation report) in consideration of the property specifying result. It can be said that the association data 109 in which the property specifying result and the selection item are associated with each other is data that records the user's tendency regarding the selection of the property item to be included in the document (interpretation report).

In the following, the process of generating the association data 109 by the association data generation unit 16 will be described with reference to FIG. 7 by taking the case where the second text T2 of the first to fourth texts T1 to T4 illustrated in FIG. 6 is selected by the user as an example.

The second text T2 includes a description "A tumor with pleural invagination is found in the left upper lobe." That is, the second text T2 is generated based on the "left upper lobe" which is the property specified for the property item "position", the "pleural invagination+" which is the property specified for the property item "presence or absence of pleural invagination", and the "tumor" which is the property specified for the property item "type of disease". In a case where the second text T2 is selected by the user, the association data generation unit 16 specifies "position", "presence or absence of pleural invagination", and "type of disease", which are property items corresponding to the properties described in the second text T2, as selection items. The association data generation unit 16 generates the association data 109 in which the specified selection items "position", "presence or absence of pleural invagination", and "type of disease" and the property specifying results "left upper lobe", "pleural invagination+", "irregular margin+", "spicula+", and "tumor", which are results of specifying the property for each of the plurality of property items in the case of generating the plurality of texts (first to fourth texts T1 to T4) including the selected second text T2, are associated with each other, and the generated association data 109 in the storage unit 103. In this case, the association data 109 indicates that the document (interpretation report) is likely to include properties relating to "position", "presence or absence of pleural invagination" and "type of disease" in a case where "left upper lobe", "pleural invagination+", "irregular margin+", "spicula+", and "tumor" are obtained as property specifying results. The association data generation unit 16 generates the association data 109 each time the plurality of texts generated by the text generation unit 14 are selected by the user, and stores the generated association data 109 in the storage unit 103. That is, the storage unit 103 stores the association data 109 in which the property specifying result and the selection item are associated with each other for the past various abnormal shadows.

At the time of generating a plurality of texts regarding the abnormal shadow included in the diagnosis target image, the text generation unit 14 accesses the storage unit 103 and determines whether or not there is association data 109 including a property specifying result that matches the property specified for the abnormal shadow included in the diagnosis target image. In a case where it is determined that there is such association data 109, the text generation unit 14 generates a text describing the property specified for the same property item as the selection item associated with the property specifying result included in the association data 109 as a priority text. The text generation unit 14 generates one or a plurality of texts in addition to the priority text. The text generation unit 14 generates the plurality of texts including the priority text such that a combination of property items corresponding to the properties described in each of the plurality of texts is different between the plurality of texts.

On the other hand, it is determined that whether or not there is no association data 109 including a property specifying result that matches the property specified for the abnormal shadow included in the diagnosis target image, the text generation unit 14 generates a plurality of texts based on a predetermined rule. The predetermined rule may be, for example, to generate texts for all combinations that select M (M<N) or more property items from among N property items. In this case, the number of property items included in each text may be different from each other or may be the same among the plurality of texts.

Figure 7:
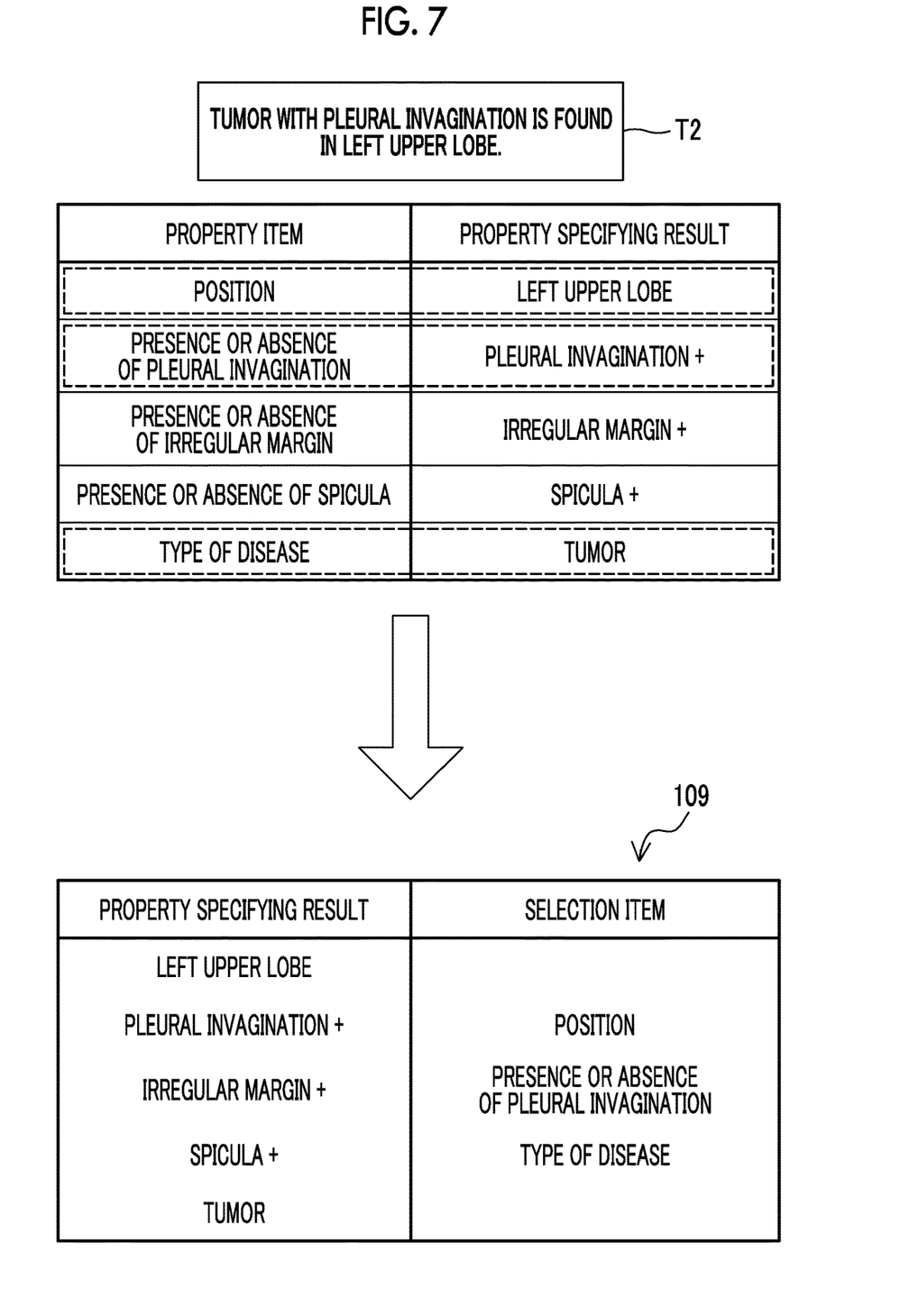
FIG. 7 is a diagram for describing a process of generating association data according to an embodiment of the disclosed technology.

For example, in a case where the association data 109 illustrated in FIG. 7 is stored in the storage unit 103, and properties specified this time for the abnormal shadow included in the diagnosis target image are "left upper lobe", "pleural invagination+", "irregular margin+", "spicula+", and "tumor", the text generation unit 14 determines that these properties specified this time match the past property specifying results included in the association data 109. In this case, in the association data 109, the text generation unit 14 generates a text including the description "A tumor with pleural invagination is found in the left upper lobe" as a priority text based on the properties "left upper lobe", "pleural invagination+", and "tumor" specified this time for the same property items as "position", "presence or absence of pleural invagination", and "type of disease", which are selection items associated with the property specifying results. In this case, a priority text including the same description as the second text T2 selected in the past is generated.

Figure 8:
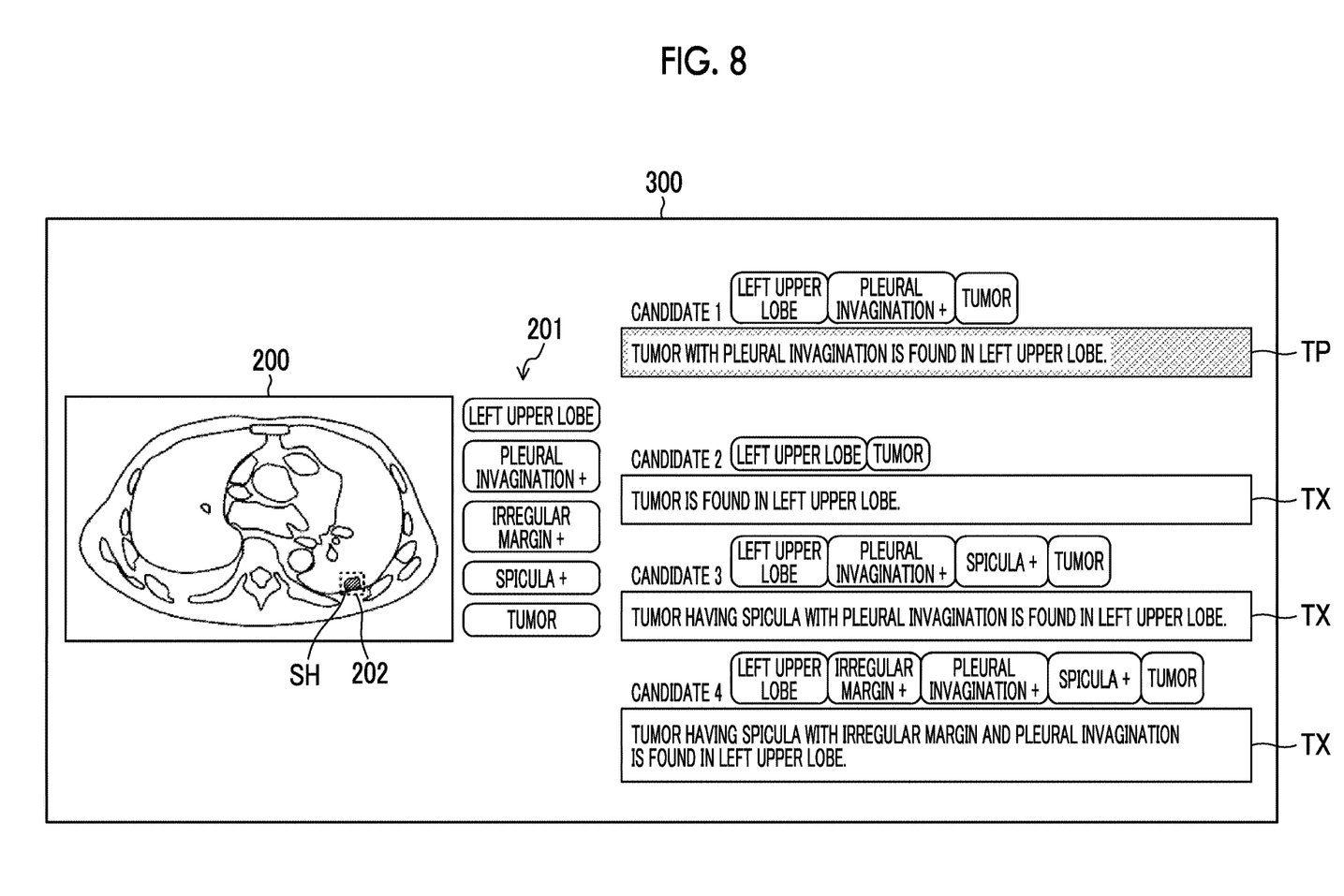
FIG. 8 is a diagram showing an example of a display form of a priority text according to an embodiment of the disclosed technology.

As described above, in a case where the priority text is included in the plurality of texts generated by the text generation unit 14, the display control unit 15 displays the priority text in an identifiable manner from other texts. FIG. 8 is a diagram showing an example of a display form of the priority text. As shown in FIG. 8, the display control unit 15 performs control such that the plurality of texts are displayed in a line in a vertical direction of the display screen 300 to locate the priority text TP at the top of the display screen 300 and the priority text TP is highlighted. FIG. 8 illustrates a case where the priority text TP is displayed in bold as highlighting and the background color of the priority text TP is displayed differently from other texts TX. The display control unit 15 may perform control such that a character or a mark indicating that the text is the priority text is displayed in the vicinity of the display region of the priority text.

Figure 9:
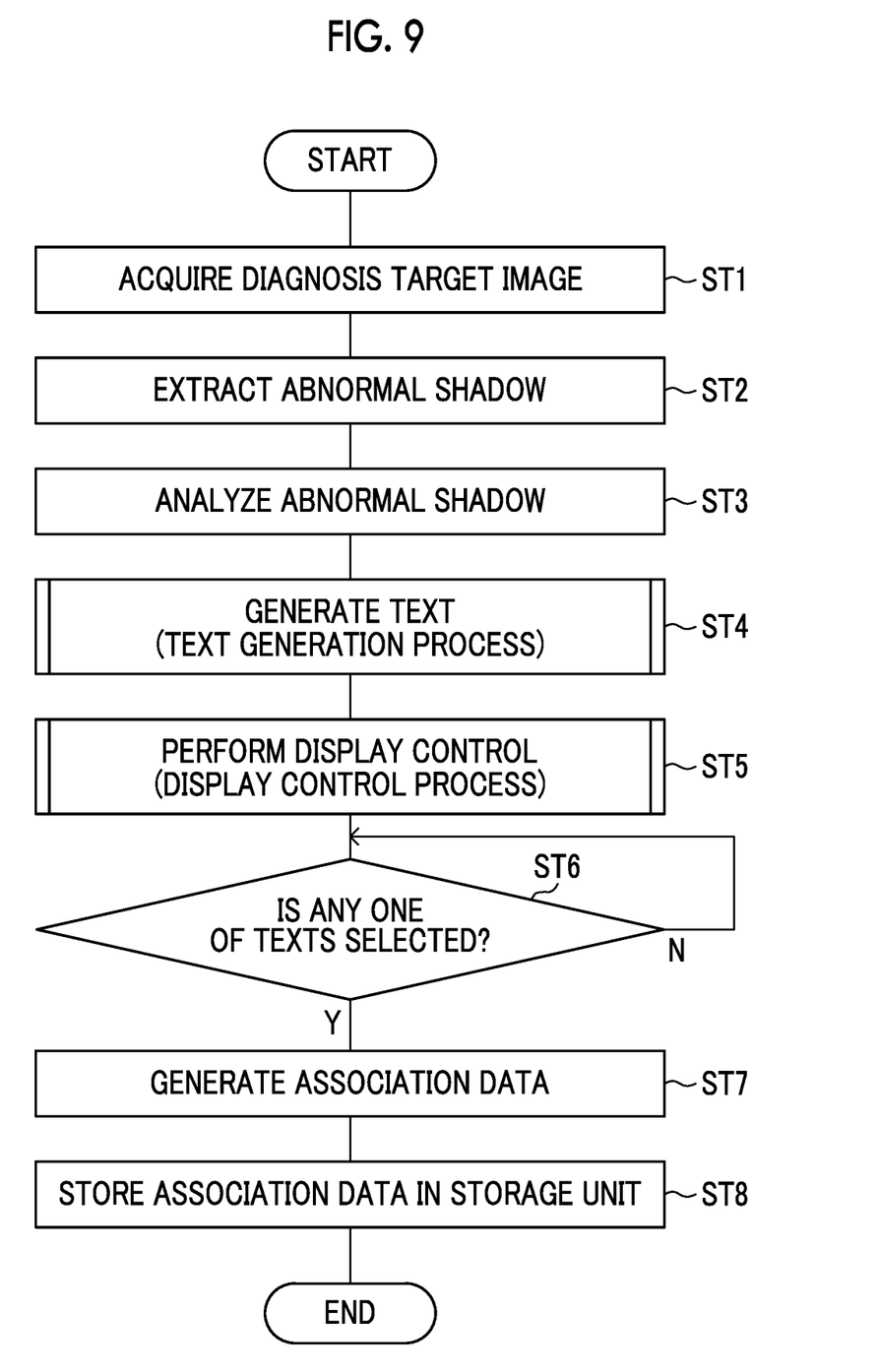
FIG. 9 is a flowchart showing an example of a flow of a document creation support process according to an embodiment of the disclosed technology.

In the following, the operation of the document creation support apparatus 10 will be described. FIG. 9 is a flowchart showing an example of a flow of a document creation support process performed by the CPU 101 executing the document creation support program 108. The document creation support program 108 is executed, for example, in a case where an instruction to start execution is input by a user via the input unit 105. It is assumed that diagnosis target image is downloaded from the image server 5 to the document creation support apparatus 10 (interpretation workstation 3) and is saved in the storage unit 103.

In Step ST1, the image acquisition unit 11 acquires the diagnosis target image saved in the storage unit 103. In Step ST2, the feature extraction unit 12 extracts abnormal shadows as feature portions from the diagnosis target image acquired by the image acquisition unit 11. In Step ST3, the analysis unit 13 analyzes the abnormal shadows extracted from the diagnosis target image, and specifies the properties of the abnormal shadow for each of the plurality of predetermined property items.

In Step ST4, the text generation unit 14 generates a plurality of different texts describing the properties specified in Step ST3. The text generation unit 14 generates the plurality of texts such that at least one of the properties specified for each of a plurality of predetermined property items is described in each of the plurality of texts and a combination of property items corresponding to the properties described in each of the plurality of texts is different between the plurality of texts.

Figure 10:
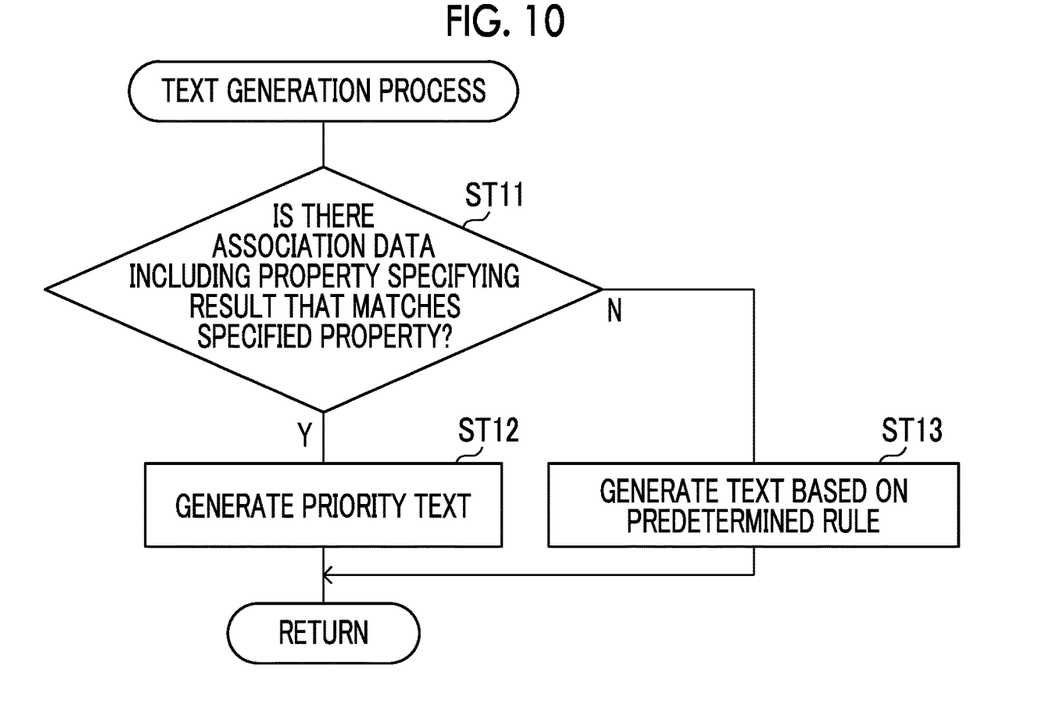
FIG. 10 is a flowchart showing an example of a flow of a text generation process according to an embodiment of the disclosed technology.

Here, FIG. 10 is a flowchart showing the details of the text generation process performed in Step ST4. In Step ST11, the text generation unit 14 accesses the storage unit 103 and determines whether or not there is association data 109 including the property specifying result that matches the property specified in Step ST3. The text generation unit 14 proceeds to the process to Step ST12 in a case where it is determined that there is such association data 109, and proceeds the process to Step ST13 in a case where it is determined that there is no such association data 109.

In Step ST12, the text generation unit 14 generates a priority text describing the property specified for the same property item as the selection item associated with the property specifying result included in the association data 109 hit in the process of Step ST11 among the properties specified in Step ST3 as one of a plurality of texts.

In Step ST13, the text generation unit 14 generates a plurality of texts based on a predetermined rule. The predetermined rule may be, for example, to generate texts for all combinations that select M (M<N) or more property items from among N property items. In this case, the number of property items included in each text may be different from each other or may be the same among the plurality of texts.

In Step ST5, the display control unit 15 performs control such that the plurality of texts generated by the text generation unit 14 are displayed on the display unit 104.

Figure 11:
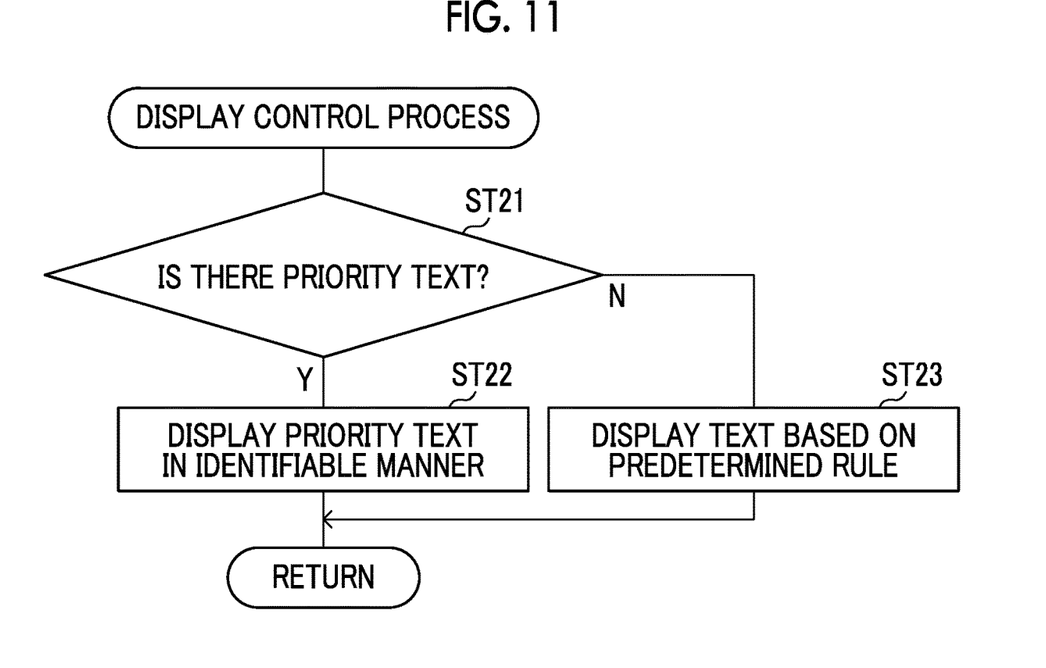
FIG. 11 is a flowchart showing an example of a flow of a display control process according to an embodiment of the disclosed technology.

Here, FIG. 11 is a flowchart showing the details of the display control process performed in Step ST5. In Step ST21, the display control unit 15 determines whether or not there is a priority text in the plurality of texts generated by the text generation unit 14. The display control unit 15 proceeds to the process to Step ST22 in a case where it is determined that there is a priority text, and proceeds the process to Step ST23 in a case where it is determined that there is no priority text.

In Step ST22, the display control unit 15 causes the priority text to be displayed on the display screen of the display unit 104 in an identifiable manner from other texts. The display control unit 15 causes the user to identify the priority text by displaying and highlighting the priority text at the top of the display screen, for example.

In Step ST23, the display control unit 15 causes a plurality of texts to be displayed on the display screen of the display unit 104 based on a predetermined rule. The predetermined rule may be, for example, to display a plurality of texts in a line in an order according to the number of property items corresponding to the properties described in the plurality of texts. The user can select any one of the plurality of texts displayed on the display unit 104 and use the selected text as a part or all of the document (interpretation report) created by the user.

In Step ST6, the association data generation unit 16 determines whether or not any one of the plurality of texts generated by the text generation unit 14 is selected.

In Step ST7, the association data generation unit 16 generates association data 109 in which a selection item, which is a property item corresponding to the property described in the text selected by the user, and a property specifying result obtained by the analysis in Step ST3 are associated with each other.

In Step ST8, the association data generation unit 16 stores the association data 109 generated in Step ST7 in the storage unit 103. Note that, in a case where it is determined that the association data 109 including the property specifying result that matches the property specified in Step ST3 is already present in the storage unit 103 in the determination of Step ST11, the association data generation unit 16 may overwrite the association data 109.

As described above, with the document creation support apparatus 10 according to the embodiment of the disclosed technology, a plurality of different texts describing the properties of the abnormal shadow extracted from the diagnosis target image are generated as candidate texts. A plurality of texts have a combination of property items corresponding to the properties described in each text that is different from each other. Accordingly, it is possible to generate a plurality of texts having a variety of description contents. As a result, there is a high likelihood that texts that match the user's request are included in the plurality of texts, and it is possible to effectively support the creation of a document (interpretation report) by the user.

Further, with the document creation support apparatus 10 according to the embodiment of the disclosed technology, in a case where any one of the plurality of generated texts is selected, the association data 109 in which a selection item, which is a property item corresponding to a property described in the selected text, and a property specifying result, which is a result of specifying the property for each of the plurality of property items in a case of generating a plurality of texts including the selected text, are associated with each other is generated. Then, in a case where the property specified for the abnormal shadow extracted from the diagnosis target image and the property specifying result included in the association data 109 match, a priority text describing the property specified for the same property item as the selection item associated with the property specifying result is generated as one of the plurality of texts. It can be said that the association data 109 in which the property specifying result and the selection item are associated with each other is data that shows the user's tendency regarding the selection of the property item to be included in the document (interpretation report).

By generating the priority text generated based on the association data 109 as one of the plurality of texts, it is possible to further increase a likelihood that texts that match the user's request are included in the plurality of texts. Further, since the priority text is displayed on the display screen in an identifiable manner from other texts, the priority text can be presented as the recommended text. In this way, by reflecting the tendency of the description content of the text selected by the user in the subsequent text generation, it is possible to increase a likelihood that texts that match the user's request are included in the plurality of candidate texts.

Further, as hardware structures of processing units that execute various kinds of processing such as each functional unit of the document creation support apparatus 10 according to the present embodiment, various processors shown below can be used. As described above, the various processors include a programmable logic device (PLD) as a processor of which the circuit configuration can be changed after manufacture, such as a field-programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are composed of one or more of the above-described various processors as hardware structures.

Furthermore, as the hardware structure of the various processors, more specifically, an electrical circuit (circuitry) in which circuit elements such as semiconductor elements are combined can be used.

The disclosure of JP2020-020866 filed on Feb. 10, 2020 is incorporated herein by reference in its entirety. Further, all literatures, patent applications, and technical standards described herein are incorporated by reference to the same extent as if the individual literatures, patent applications, and technical standards were specifically and individually stated to be incorporated by reference.

What is claimed is:

1. A document creation support apparatus comprising at least one processor,
wherein the processor is configured to
acquire an image;
perform imaging processing on the image to detect an abnormal shadow in the image;
analyze the abnormal shows detected from the image and specify properties of the abnormal shadow for each of a plurality of property items to generate property specifying results, wherein each of the property specifying results is a specified result corresponding to a different one of the plurality of property items;
generate a set of a plurality of texts in a manner that different combinations of property specifying results are described in each plurality of texts of the set of plurality of texts;
generate a graphical user interface and display each plurality of texts of the set of plurality of texts in a separate box of a plurality of boxes in the graphical user interface;
receive an input to select one of the plurality of boxes and adopt the plurality of texts in the set of the plurality of texts in the selected box as a part of an interpretation report;

in a case where an input is received to select any one of the plurality of boxes, update association data in which one or more property items of the plurality of property items corresponding to each property described in the selected box, and one or more property specifying results of the property specifying results described in the selected box are associated with each other, wherein generate the graphical user interface and display each plurality of texts of the set of plurality of texts in separate box of the plurality of boxes in the graphical user interface comprising:
  determine, based on the association data, whether one or more property specifying results described in a box of the multiple boxes match each specified properties of the detected abnormal shadow, and
  display a plurality of text corresponding to the box as a priority text in response to having determined that the one or more property specifying results described in the box having matched each specified properties of the detected abnormal shadow based on the association data.

2. The document creation support apparatus according to claim 1, wherein the processor is configured to, in a case where each of the plurality of texts is displayed on the graphical user interface of a display screen, perform control such that the priority text in the box is displayed in an identifiable manner from other texts in other boxes of the plurality of boxes.

3. The document creation support apparatus according to claim 2, wherein the processor is configured to perform control such that the plurality of texts are displayed in a line in a vertical direction of the display screen to locate the priority text at a top of the display screen.

4. The document creation support apparatus according to claim 2, wherein the processor is configured to perform control such that the priority text is highlighted.

5. The document creation support apparatus according to claim 1, the processor is configured to update the association data each time any one of the plurality of texts is selected, and store the updated association data in a storage unit.

6. A document creation support method comprising:
  acquiring an image;
  performing imaging processing on the image to detect an abnormal shadow in the image;
  analyzing the abnormal shows detected from the image and specify properties of the abnormal shadow for each of a plurality of property items to generate property specifying results, wherein each of the property specifying results is a specified result corresponding to a different one of the plurality of property items;
  generating a set of a plurality of texts in a manner that different combinations of property specifying results are described in each plurality of texts of the set of plurality of texts;
  generating a graphical user interface and display each plurality of texts of the set of plurality of texts in a separate box of a plurality of boxes in the graphical user interface;
  receiving an input to select one of the plurality of boxes and adopt the plurality of texts in the set of the plurality of texts in the selected box as a part of an interpretation report;
  in a case where an input is received to select any one of the plurality of boxes, updating association data in which one or more property items of the plurality of property items corresponding to each property described in the selected box, and one or more property specifying results of the property specifying results described in the selected box are associated with each other, wherein generate the graphical user interface and display each plurality of texts of the set of plurality of texts in separate box of the plurality of boxes in the graphical user interface comprising:
  determining, based on the association data, whether one or more property specifying results described in a box of the multiple boxes match each specified properties of the detected abnormal shadow, and
  displaying a plurality of text corresponding to the box as a priority text in response to having determined that the one or more property specifying results described in the box having matched each specified properties of the detected abnormal shadow based on the association data.

7. A non-transitory computer-readable storage medium storing a program for causing a computer to execute a process comprising:
  acquiring an image;
  performing imaging processing on the image to detect an abnormal shadow in the image;
  analyzing the abnormal shows detected from the image and specify properties of the abnormal shadow for each of a plurality of property items to generate property specifying results, wherein each of the property specifying results is a specified result corresponding to a different one of the plurality of property items;
  generating a set of a plurality of texts in a manner that different combinations of property specifying results are described in each plurality of texts of the set of plurality of texts;
  generating a graphical user interface and display each plurality of texts of the set of plurality of texts in a separate box of a plurality of boxes in the graphical user interface;
  receiving an input to select one of the plurality of boxes and adopt the plurality of texts in the set of the plurality of texts in the selected box as a part of an interpretation report;
  in a case where an input is received to select any one of the plurality of boxes, updating association data in which one or more property items of the plurality of property items corresponding to each property described in the selected box, and one or more property specifying results of the property specifying results described in the selected box are associated with each other, wherein generate the graphical user interface and display each plurality of texts of the set of plurality of texts in separate box of the plurality of boxes in the graphical user interface comprising:
  determining, based on the association data, whether one or more property specifying results described in a box of the multiple boxes match each specified properties of the detected abnormal shadow, and
  displaying a plurality of text corresponding to the box as a priority text in response to having determined that the one or more property specifying results described in the box having matched each specified properties of the detected abnormal shadow based on the association data.

* * * * *